United States Patent [19]

Cholod

[11] 4,130,580
[45] Dec. 19, 1978

[54] SODIUM ION REMOVAL FROM ACETONE CYANOHYDRIN

[75] Inventor: Michael Cholod, Cornwells Heights, Pa.

[73] Assignee: Rohm and Haas Company, Philadelphia, Pa.

[21] Appl. No.: 848,166

[22] Filed: Nov. 3, 1977

[51] Int. Cl.$^2$ ............................................. C07C 121/36
[52] U.S. Cl. ...................................................... 260/465.6
[58] Field of Search ....................................... 260/465.6

[56] References Cited

U.S. PATENT DOCUMENTS

| 2,444,589 | 7/1948 | Blann | 260/465.6 |
|---|---|---|---|
| 2,537,814 | 1/1951 | Davis | 260/465.6 |
| 2,982,779 | 5/1961 | Fierce et al. | 260/465.6 X |
| 3,700,718 | 10/1972 | Yamagishi et al. | 260/465.6 |

FOREIGN PATENT DOCUMENTS

| 479652 | 12/1951 | Canada | 260/465.6 |
|---|---|---|---|
| 737990 | 7/1966 | Canada | 260/465.6 |
| 50-111020 | 1/1975 | Japan | 260/465.6 |
| 471952 | 9/1937 | United Kingdom. | |
| 248654 | 12/1969 | U.S.S.R. | 260/465.6 |

Primary Examiner—Joseph Paul Brust
Attorney, Agent, or Firm—Jordan J. Driks

[57] ABSTRACT

In a process for the preparation of acetone cyanohydrin by the reaction of acetone and hydrocyanic acid in the presence of a sodium hydroxide catalyst, the method of removal of corrosion inducing sodium ion during the purification of the crude acetone cyanohydrin, involving the steps of (1) passing a cooled crude acetone cyanohydrin feedstream through a cationic ion exchange resin to remove substantially all of the sodium ion; (2) regenerating exhausted ion exchange resin; (3) acidifying the substantially sodium ion-free crude feedstream to a pH of 1.5–2.0 to stabilize said crude acetone cyanohydrin; (4) feeding the acidified substantially sodium ion-free crude feedstream to a first concentrator; (5) removing overhead, from the first concentrator, unreacted acetone and sending the bottoms from said first concentrator to a second concentrator; and (6) removing purified acetone cyanohydrin as bottoms from the second concentrator and recycling the overhead for further generation of acetone cyanohydrin.

4 Claims, 1 Drawing Figure

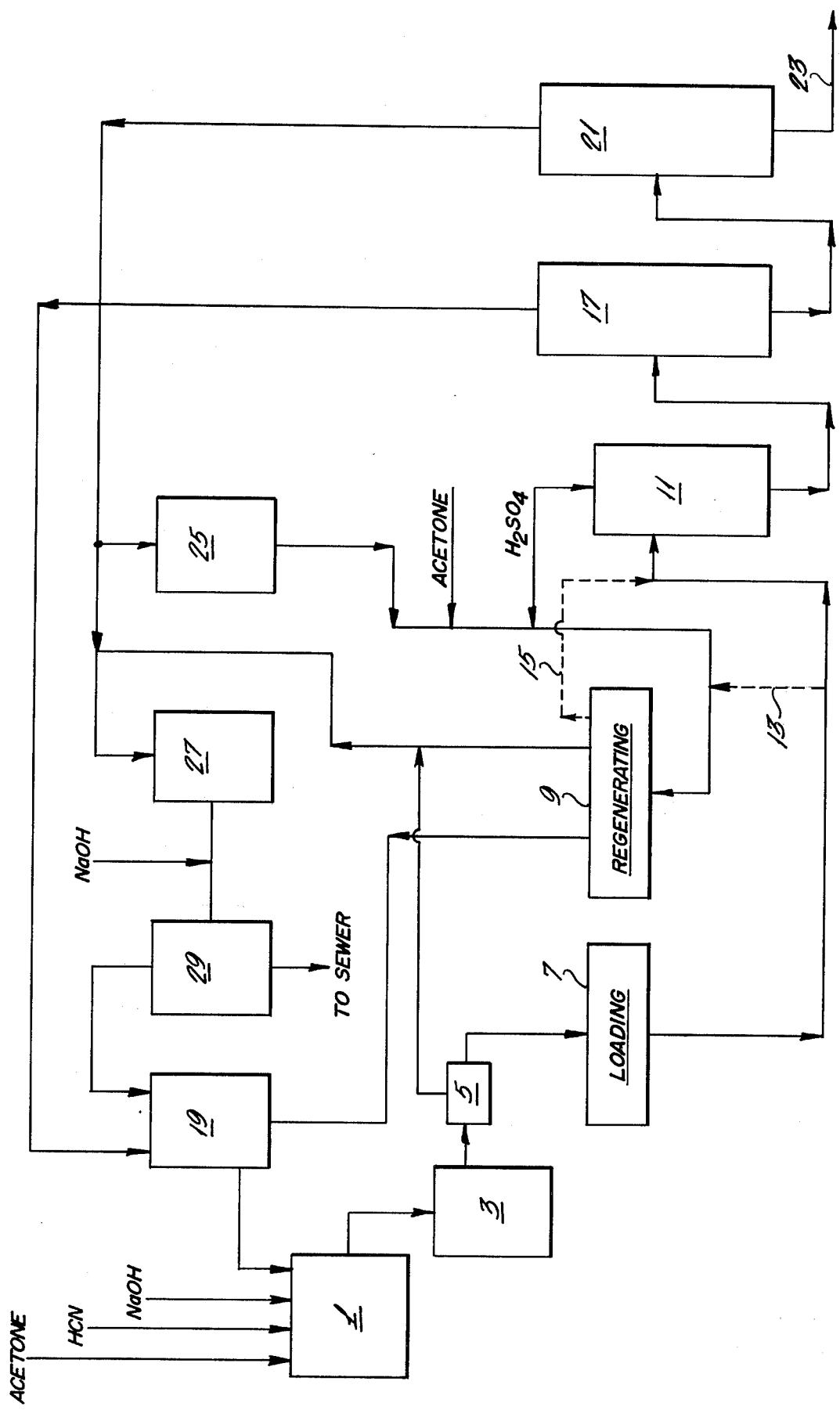

SODIUM ION REMOVAL FROM ACETONE CYANOHYDRIN

This invention relates generally to a process for the production and purification of acetone cyanohydrin.

Acetone cyanohydrin is generally produced by an addition reaction of hydrocyanic acid and acetone in the presence of an alkaline catalyst, which is most often sodium hydroxide. The acetone cyanohydrin so prepared contains small quantities of unreacted acetone and hydrocyanic acid as well as small quantities of sodium ion from the catalyst. This acetone cyanohydrin, therefore, requires purification in order to remove all unreacted material and impurities. However, such a purification is not readily accomplished. Any scheme in which hydrocyanic acid is removed from the crude product must involve a step for detoxifying any hydrocyanic acid-containing waste streams before sending them to waste disposal. Moreover, both unreacted acetone and hydrocyanic acid are recyclable and can be used for further acetone cyanohydrin generation. A more severe problem is presented by the sodium ion. This ion is capable of inducing severe corrosion in the various parts of the purification and recovery equipment and its removal is imperative in order to have acceptable equipment life. Heretofore, methods have been derived to remove this undesirable sodium ion, such as by addition of sulfuric acid to precipitate sodium sulfate and thereby remove sodium ion. However, by this method, sodium ion is still present in sufficient quantity to cause corrosion. Moreover, the sodium sulfate precipitate must be completely removed, otherwise the material will accumulate in and clog recovery equipment pipes, pumps and so forth.

It has now been found that acetone cyanohydrin can be purified by a process in which acetone cyanohydrin is recovered in high yields, all unreacted reactants are recycled with only one stream free of toxic materials being sent to waste disposal, and substantially all sodium ion is removed from the crude acetone cyanohydrin. In this process for the preparation of acetone cyanohydrin by the reaction of acetone and hydrocyanic acid in the presence of a sodium hydroxide catalyst, the method of removal of corrosion inducing sodium ion during the purification of crude acetone cyanohydrin comprises the steps of (1) passing a cooled crude acetone cyanohydrin feedstream through a cationic ion exchange resin to remove substantially all of the sodium ion; (2) regenerating exhausted ion exchange resin; (3) acidifying the substantially sodium ion-free crude feedstream to a pH of 1.5–2.0 to stabilize the crude acetone cyanohydrin; (4) feeding the acidified substantially sodium ion-free crude feedstream to a first concentrator; (5) removing overhead, from the first concentrator, unreacted acetone and sending the bottoms to a second concentrator; and (6) removing purified acetone cyanohydrin as bottoms from the second concentrator and recycling the overhead for further generation of acetone cyanohydrin.

Acetone cyanohydrin is generally prepared by mixing acetone, hydrocyanic acid, water and a sodium hydroxide catalyst at about $-10°$ to about $50°$ C. in an acetone cyanohydrin generator. The crude acetone cyanohydrin is then passed to a holding tank to obtain equilibrium and to cool the crude feedstream. At this point the crude acetone cyanohydrin is stabilized by the addition of sulfuric acid. The stabilized crude feedstream is filtered, and the filtrate concentrated in several stages to yield purified acetone cyanohydrin containing about 100–600 ppm. of sodium ion. It is this very sodium ion, however, which is responsible for the severe corrosion which occurs in the acetone cyanohydrin purification and recovery equipment, especially in the waste heat boilers. It has been found that it is now possible to remove substantially all sodium ion from filtered holding tank effluent by means of an ion exchange system.

In the ion exchange system, the crude cooled, stabilized acetone cyanohydrin feedstream is first filtered and then passed through an ion exchange resin to remove substantially all of the sodium ion. In a preferred system, two ion exchange resin columns are arranged in parallel, so that one column is used to remove sodium ion, while the other is regenerated. When the first column is exhausted, the feedstream is switched to the regenerated column, and the exhausted column is itself regenerated. The useful ion exchange resins include the cationic resins and most preferably macroreticular cation ion exchange resins, such as those sold under the trade designation Amberlyst 15 and Amberlite 200 and the like.

Under actual process conditions, the feedstream is passed through one column until such time as the sodium leakage level, or amount of sodium being allowed to pass through the column, reaches a predetermined level. Thus, for example, a feedstream containing $>$ 100 ppm. of sodium ion is passed through the column until the exiting feedstream exhibits sodium ion levels of about 50 ppm. At this point, the column is considered exhausted and the column is taken off-stream, and the feedstream switched to a fresh or regenerated column.

The regeneration of exhausted ion exchange resins is conducted using an acidified regenerant. The regeneration process begins by rinsing the exhausted column with acetone, the used regeneration acetone being recycled to the acetone cyanohydrin generator. This acetone rinse is followed by a water rinse. The column is then regenerated by passing acidified water through the column. In the preferred process, regeneration is carried out using 5% sulfuric acid in water or in the overheads from the second acetone cyanohydrin concentrator. This overhead from the second concentrator is largely water, so that acidified second concentrator overheads are highly suitable as a regenerant. The regeneration is conducted so as to minimize excess acid in the effluent by adjusting the amount of regenerant feed so that regeneration proceeds only to the point where regenerant acid begins to leak through the column. In this manner, excess acid requiring expensive neutralization and disposal is greatly minimized. Stoichiometric regeneration can be accomplished by monitoring sodium ion leakage during column loading and then regenerating at a predetermined sodium ion leakage level. Also, monitoring acid break-through during regeneration can be used to achieve stoichiometric acid utilization.

After regeneration, the column is water and acetone rinsed, after which it is ready to be put back onstream. The regeneration streams with high water, sodium ion and acid contents are neutralized with a base, such as sodium hydroxide and sent to an acetone recovery still. In this still, the organics (acetone and hydrocyanic acid) are taken overhead and recycled to the acetone cyanohydrin generator. The detoxified water and the salts which are innocuous, are sent to the sewer. Because this regeneration sequence uses only materials inherent in the entire process (acetone and second concentrator overhead), the addition of small stoichiometric amounts of acid, such as sulfuric acid, and water, minimize regeneration costs and all expended regeneration liquids are disposed of within the preparation and purification process.

The substantially sodium ion-free acetone cyanohydrin is then acidified, preferably to a pH of 1.5–2.0. Acetone cyanohydrin is sensitive to cleavage in an alkaline medium, and as a result, it is necessary to stabilize it by adjusting the pH to from about 1.5 to about 2.0.

The stabilized, substantially sodium ion-free acetone cyanohydrin is then distilled and thereby concentrated, using a two stage concentration process. In the first distillation or concentrator, any unreacted reactants left in the crude feedstream are removed overhead and recycled to the acetone cyanohydrin generator while the bottoms containing remaining unreacted acetone, some water and the acetone cyanohydrin, are fed to the second concentrator. In the latter, the water and acetone are removed overhead and partly recycled to the acetone cyanohydrin generator, with the remainder being acidified and used as ion exchange column regenerant. The bottoms from the second concentrator contain acetone cyanohydrin in < 99% concentration.

The present invention is illustrated in more detail with reference to the accompanying drawing which schematically depicts the process in the form of a flow chart.

The reactants and catalyst are reacted in the acetone cyanohydrin generator 1. The crude acetone cyanohydrin feedstream is fed from the acetone cyanohydrin generator 1 to a hold tank 3, where the crude feedstream is allowed to cool and come to an equilibrium. This crude feedstream, containing approximately 70% acetone cyanohydrin, 18% acetone, 10% water and 100–600 ppm. of sodium ion is then fed to a filtration unit 5 for filtration. The filter bed is washed with water and the washings are sent to the acetone recovery holding tank 27. The filtered crude acetone cyanohydrin feedstream is then sent to a loading ion exchange resin column 7, where it is passed through the column to remove substantially all of the sodium ion. The column 7 is loaded, until sodium ion leakage reaches a predetermined level at which the column is considered to be exhausted. At this point the feedstream is rerouted to the regenerated column 9. The substantially sodium ion-free feedstream leaves the column 9 and is sent to the neutralization tank 11. In this flow chart, phantom lines 13 and 15 represent the flow of the acetone cyanohydrin feedstream through column 9 when the latter is used as the loading column. The solid lines represent the loading of column 7 and the regeneration of column 9.

The substantially sodium ion-free feedstream is sent from the column 7 to the neutralization tank 11. Here, the crude acetone cyanohydrin feedstream is stabilized by the addition of sulfuric acid to adjust the pH of the feedstream to about 1.5–2.0. The stabilized feedstream is then sent to the first concentrator 17. Here, the feedstream, containing about 8% acetone, 8% water, and 82% acetone cyanohydrin is distilled to take overhead a major portion of the acetone and water, which are sent to the tank 19 for recovered acetone. The bottoms, containing about 97% acetone cyanohydrin, 2% water and 1% acetone, are sent to the second concentrator 21. Here, all but a small fraction (< 1.0%) of the water and remaining acetone are taken overhead, and > 99% pure acetone cyanohydrin product is removed as bottoms via line 23.

The overhead from the second concentrator 21 is fed partly to an overhead hold tank 25. The remainder of the overhead is fed to the acetone recovery tank 27. The material in the acetone recovery tank 27, which includes some acetone cyanohydrin, acetone, water and sodium ion, is neutralized with sodium hydroxide. In this alkaline environment, the acetone cyanohydrin is cleaved into its components, acetone and hydrocyanic acid. This neutralized feedstream is fed to the acetone recovery column 29. The overheads from this column containing acetone and hydrocyanic acid, are fed to the recovered acetone tank 19, from which all recycled organic components are recycled back to the acetone cyanohydrin generator 1, for further production of acetone cyanohydrin. The detoxified water and salts, which emanate from the bottoms of the acetone recovery column 29, are flushed to the sewer.

The regeneration process is carried out by first rinsing the exhausted column (in the flow chart indicated as 9) with acetone, followed by the regenerant, comprising the overhead from the second concentrator 21, being held in the overhead hold tank 25. This overhead is acidified with sulfuric acid and fed to the column 9. Finally, the column 9 is again rinsed with acetone. All used rinse and regenerant streams are fed to the acetone recovery tank 27 for further processing and recycling to the acetone cyanohydrin generator 1.

The process of this invention can be further understood from the following examples, which are illustrative of but not limiting of the process.

EXAMPLE 1

Two 18 in. lengths of 1 inch diameter glass pipe are each filled to a depth of about 1 ft. with 155 milliliters of Amberlyst 15 in the acid form. Crude acetone cyanohydrin containing 136 parts per million of sodium ion is passed down through one of the columns containing the Amberlyst 15. Samples of acetone cyanohydrin exiting from the column are periodically removed and measured for sodium ion leakage using flame photometry. When the amount of sodium ion leaving the glass column reaches the level of 50 parts per million, the flow of acetone cyanohydrin is transferred to the second glass column containing Amberlyst 15 in the acid form.

During the time that the crude acetone cyanohydrin is being passed through the second column, the Amberlyst 15 resin in the first column is regenerated by backwashing the resin with acetone at a rate of 25 to 50 cc. per minute. The backwash is accomplished with 6 to 12 bed volumes of acetone (one bed volume equals 155 milliliters) until the bed of Amberlyst 15 resin expands to fill the column. Thereafter, half a bed volume of acetone and half a bed volume of water is backwashed through the first column, at a rate of 4 bed volumes per hour, followed by half a bed volume of 5% aqueous sulfuric acid regenerant. The regeneration procedure is then completed,, at a rate of 4 bed volumes per hour, with two bed volumes of water, half a bed volume of acetone and 1.7 bed volumes of sodium free crude acetone cyanohydrin. The first column is then ready to accept additional sodium ion containing acetone cyanohydrin when the second column containing Amerlyst 15 is exhausted as indicated by the detection of leakage through the column of at least 50 parts per million of sodium ion. 96.5% of the sodium ion is removed from the crude acetone cyanohydrin.

EXAMPLE 2

Crude acetone cyanohydrin containing 156 parts per million of sodium is treated, in the manner of Example 1, for a total of 6 column loading/column regeneration combinations. The average through put per column, prior to regeneration, is 66.4 bed volumes of crude acetone cyanohydrin at a flow rate of 6.7 bed volumes per hour. An average of 70.6 meq. of sodium ion is removed per column, prior to regeneration, with an average sodium ion leakage of 4.8 parts per million. Resin bed regeneration is accomplished, in the manner of Example 1, using 0.51 bed volumes of 5% aqueous sulfuric acid. An average of 96.9% of sodium ion is removed from the crude acetone cyanohydrin.

EXAMPLE 3

Example 3 differs from Example 1 in that a ¾ inch diameter glass pipe is used instead of the 1 inch glass pipe of Example 1. One bed volume in Example 3 is equivalent to 40.8 milliliters.

The procedure of Example 1 is repeated except that crude acetone cyanohydrin containing 469 parts per million of sodium ion is treated for 6 column loading-/column regeneration procedures. The average through put per column is 25.5 bed volumes at a flow rate of 8.3 bed volumes per hour. An average of 23 meq. of sodium ion is removed per column during each cycle with an average sodium ion leakage of 7.3 parts per million. Resin bed regeneration is accomplished with 0.57 bed volume of 5% aqueous sulfuric acid. 98.4% of the sodium ion present is removed from the crude acetone cyanohydrin.

EXAMPLE 4

Example 4 differs from Example 1 in that a ¾ inch diameter glass pipe is used instead of the 1 inch glass pipe of Example 1. One bed volume in Example 4 is equivalent to 40.8 milliliters.

Crude acetone cyanohydrin containing 940 parts per million sodium ion is treated by the procedure of Example 1 for a total of 8 column loading/column regeneration procedures. The average through put per column is 20.2 bed volumes at an average flow rate of 7.8 bed volumes per hour. An average of 36.9 meq. of sodium ion is removed per column, per cycle, with an average sodium ion leakage of 4.1 parts per million for each cycle. The resin bed regeneration is accomplished in the manner of Example 1. 99.6% of the sodium ion present is removed from the crude acetone cyanohydrin.

While this invention has been described in terms of certain preferred embodiments and illustrated by means of specific Examples, the invention is not to be construed as limited except as set forth in the following claims.

I claim:

1. In a process for the preparation of acetone cyanohydrin by the reaction of acetone and hydrocyanic acid in the presence of a sodium hydroxide catalyst, the method of removal of corrosion inducing sodium ion during purification of crude acetone cyanohydrin, comprises the steps of
    (a) passing a cooled, crude acetone cyanohydrin feedstream through a cationic ion exchange resin in the acid form to remove substantially all of said sodium ion;
    (b) regenerating exhausted ion exchange resin;
    (c) acidifying said substantially sodium ion-free crude feedstream to a pH of 1.5–2.0 to stabilize said crude acetone cyanohydrin;
    (d) feeding said acidified substantially sodium ion-free crude feedstream to a first concentrator;
    (e) removing overhead from said first concentrator unreacted acetone and sending the bottoms from said first concentrator to a second concentrator; and
    (f) removing purified acetone cyanohydrin as bottoms from said second concentrator and recycling the overhead from said second concentrator for further generation of acetone cyanohydrin.

2. The process of claim 1, wherein said removal of sodium ion is carried out in a two column ion exchange system, by passing said feedstream through a first column until said first column is exhausted, said first column then being taken off-stream and regenerated and rerouting said feedstream through the second column thereby continuing the active removal of sodium ion from said feedstream.

3. The process of claim 2, wherein said regeneration comprises
    (a) eluting acetone through said exhausted ion exchange resin column;
    (b) recycling said acetone to the acetone cyanohydrin generator;
    (c) regenerating said eluted column with an acidified water wash stream;
    (d) neutralizing said regeneration wash stream; and
    (e) sending said neutralized wash stream to a recovery still wherein organic material taken overhead is recycled to the acetone cyanohydrin generator and bottoms from said recovery still are discarded.

4. The process of claim 3, wherein the acidified water wash stream comprises the acidified overhead from the second concentrator.

* * * * *

UNITED STATES PATENT AND TRADEMARK OFFICE
CERTIFICATE OF CORRECTION

PATENT NO. : 4,130,580
DATED : December 19, 1978
INVENTOR(S) : Michael Cholod

It is certified that error appears in the above—identified patent and that said Letters Patent are hereby corrected as shown below:

Col. 3, line 26 - symbol "less than ($<$)" should read -- more than ($>$) --.

Col. 4, line 59 - after word "completed" delete second comma (,).

Signed and Sealed this

Twenty-sixth Day of February 1980

[SEAL]

Attest:

SIDNEY A. DIAMOND

Attesting Officer      Commissioner of Patents and Trademarks